United States Patent
Lürssen et al.

(10) Patent No.: US 12,419,768 B2
(45) Date of Patent: Sep. 23, 2025

(54) JOINT FOR AN ANKLE ORTHOSIS

(71) Applicant: Ottobock SE & Co. KGAA, Duderstadt (DE)

(72) Inventors: Marcus Lürssen, Göttingen (DE); André Müller, Duderstadt (DE); Norbert Schimek, Kirchworbis (DE); Marcel Jung, Duderstadt (DE); Olaf Kroll-Orywahl, Northeim (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 974 days.

(21) Appl. No.: 17/413,379

(22) PCT Filed: Dec. 11, 2019

(86) PCT No.: PCT/EP2019/084615
§ 371 (c)(1),
(2) Date: Jun. 11, 2021

(87) PCT Pub. No.: WO2020/120559
PCT Pub. Date: Jun. 18, 2020

(65) Prior Publication Data
US 2022/0031491 A1    Feb. 3, 2022

(30) Foreign Application Priority Data
Dec. 12, 2018 (DE) .................. 102018131929.0

(51) Int. Cl.
*A61F 5/01* (2006.01)

(52) U.S. Cl.
CPC .... *A61F 5/0127* (2013.01); *A61F 2005/0165* (2013.01); *A61F 2005/0169* (2013.01); *A61F 2005/0179* (2013.01)

(58) Field of Classification Search
CPC ...... A61F 2005/0179; A61F 2005/0165; A61F 2005/0169; A61F 5/0127
See application file for complete search history.

(56) References Cited

U.S. PATENT DOCUMENTS 2,591,373 A * 4/1952 Methodius ................ A61F 2/64
                                                        623/44
4,958,643 A * 9/1990 Pansiera ............... A61F 5/0125
                                                        16/375
(Continued)

FOREIGN PATENT DOCUMENTS

CN    105464733 A    4/2016
CN    107858206 A    3/2018
(Continued)

OTHER PUBLICATIONS

English version, U.S. Pat. No. 10201014334 B4 2023.*
(Continued)

*Primary Examiner* — Camtu T Nguyen
(74) *Attorney, Agent, or Firm* — HOLLAND & HART LLP

(57) ABSTRACT

The invention relates to a joint for an orthopedic device, wherein the joint includes a first element with at least one end stop element and a second element which is mounted on the first element such that it can be swivelled and has at least one contact surface that can be brought into contact with the at least one end stop element by swivelling the second element relative to the first element, wherein the at least one end stop element then counters a further swivelling of the second element relative to the first element with a force, wherein at least one contact element is fixed on the second element such that it can be detached, said contact element having at least one contact surface.

17 Claims, 4 Drawing Sheets

(56) References Cited

U.S. PATENT DOCUMENTS

| | | | | |
|---|---|---|---|---|
| 5,399,149 | A | * | 3/1995 | Frankowiak .......... A61F 5/0125 403/322.2 |
| 6,165,226 | A | * | 12/2000 | Wagner ................. A61F 5/0125 623/46 |
| 2004/0002672 | A1 | * | 1/2004 | Carlson ................. A61F 5/0127 602/16 |
| 2004/0067095 | A1 | | 4/2004 | Pansiera |
| 2006/0173392 | A1 | | 8/2006 | Turrini |
| 2008/0082031 | A1 | | 4/2008 | Nathanson |
| 2016/0361189 | A1 | | 12/2016 | Campbell et al. |
| 2018/0289523 | A1 | * | 10/2018 | Fujikake ............... A61F 5/0127 |

FOREIGN PATENT DOCUMENTS

| | | |
|---|---|---|
| CN | 207882022 U | 9/2018 |
| DE | 29902609 U1 | 7/1999 |
| DE | 102015112283 A1 | 2/2017 |
| DE | 10 2010 014 334 B4 * | 8/2023 |
| WO | 2016201318 A1 | 12/2016 |

OTHER PUBLICATIONS

International Search Report and Written Opinion issued in PCT/EP2019/084615 on Mar. 23, 2020, 7 pgs.

Chinese Patent Application No. 201980081794.X; Decision of Rejection dated Nov. 16, 2023; 9 pgs.

* cited by examiner

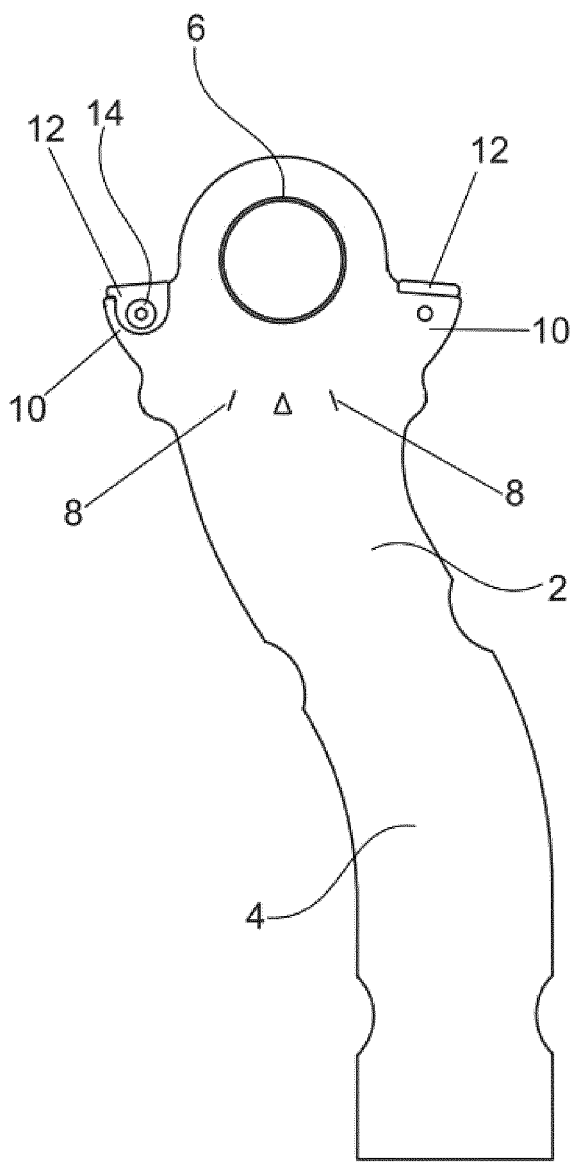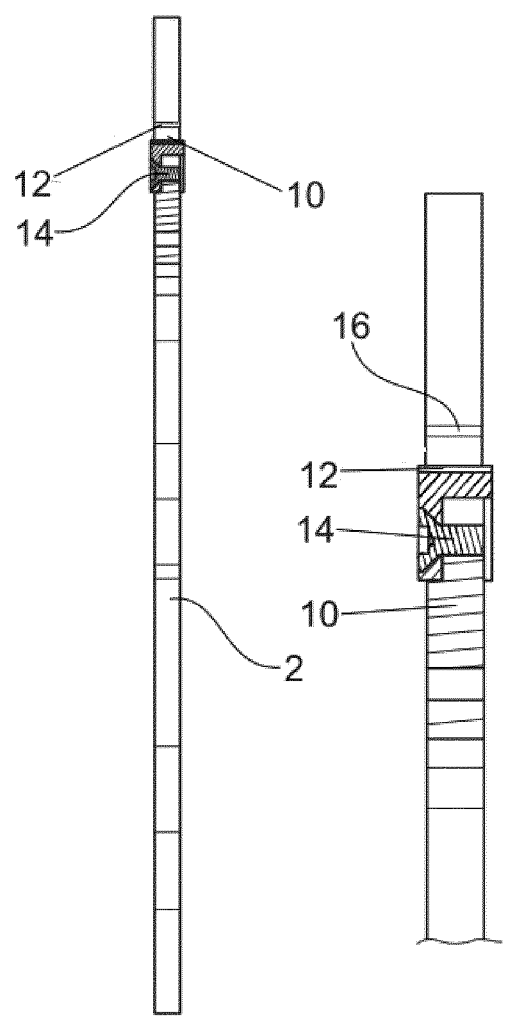
Fig. 1  Fig. 2  Fig. 3

JOINT FOR AN ANKLE ORTHOSIS

CROSS-REFERENCE TO RELATED APPLICATIONS

This is a national stage application of International Application No. PCT/EP2019/084615, filed 11 Dec. 2019, which claims the benefit of German Patent Application No. 102018131929.0, filed 12 Dec. 2018, the disclosures of which are incorporated, in their entireties, by this reference.

TECHNICAL FIELD

The invention relates to a joint for an orthopedic device, wherein the joint comprises a first element with at least one end stop element and a second element which is mounted on the first element such that it can be swivelled and has at least one contact surface that can be brought into contact with the at least one end stop element by swivelling the second element relative to the first element, wherein the at least one end stop element then counters a further swivelling of the second element relative to the first element with a force.

BACKGROUND

Such a joint for an ankle orthosis is known from DE 10 2010 014 334 A1, for example.

In the present context, an ankle orthosis is understood to mean all orthoses that bridge the ankle of a lower limb. In the present context, an ankle orthosis is also understood to mean leg and lower leg orthoses insofar as they also have a foot part and therefore bridge the human ankle.

With such ankle orthoses, the first element is normally a lower leg element and the second element a foot stirrup. The reverse configuration is of course also possible. The lower leg element is preferably to be fixed to the lower leg of the wearer of the ankle orthosis. To this end, it may feature a strap, for example, that is placed around the lower leg. However, the lower leg element of the joint may also just be a fixing element on which a further lower leg element, such as a lower leg rail, can be arranged. The foot stirrup can be designed as a single piece with a foot part which is arranged, for example, under the sole of the wearer of the ankle orthosis, or it may be merely a fixing element on which a corresponding foot part can be arranged.

It may be practical for therapeutic reasons to restrict the length of the swivel movement, i.e. the maximum possible swivel angle between the lower leg element and the foot stirrup, and, for example, to provide an end stop in one or both directions. In order to prevent too hard of a strike of these end stops, they are often designed to be spring-loaded and thus damped. Particularly in these designs, but also without being equipped with end stops, ankle orthoses and especially their joints are exposed to great mechanical stresses during use when walking. This may cause wear, damage and malfunctions.

When the orthopedic device is in the mounted state, the second element is swivelled relative to the first element when, for example, the wearer of the orthopedic device performs a certain movement, such as bending a knee or taking a step. At a certain position of the first element relative to the second element, the contact surface of the second element comes into contact with the end stop element. A further swivelling in the same direction results in a force opposite to the swivelling. This force can be overcome with a spring-loaded or damped end stop element so that further swivelling is possible. In the case of a fixed or static end stop, the force cannot be overcome without damaging the joint. This force is applied by the end stop element.

SUMMARY

The invention aims to eliminate these disadvantages or at least to reduce them.

The invention solves the problem by way of a joint for an orthopedic device according to the preamble of claim 1, which is characterized in that at least one contact element is fastened to the second element such that it can be detached, said contact element comprising at least one contact surface.

In the embodiment according to the invention, the point at which the force applied by the at least one end stop element is introduced into the second element is formed by the contact surface of the at least one contact element. At this point, the wear and tear and damage known from the prior art may occur. Since the at least one contact element is arranged on the second element such that it can be detached, it is easy to replace so that the joint can be repaired particularly easily. For this purpose, it may be sufficient to disassemble the joint once, remove the at least one contact element from the second element and to detachably arrange an intact contact element back on the second element. Conventionally, individually produced orthosis elements are arranged on the first element and the second element of the joint for the orthopedic device, said orthosis elements being adjusted to the wearer of the orthosis. To ensure that an adjustment, positioning and orientation of the different components relative to each other when the orthosis is worn are not lost once they have been selected, these components are generally connected to the first element and the second element in such a way that they cannot be detached. This is achieved, for example, by casting the first element and/or the second element in the corresponding component or glueing it to the component.

If wear leads to deformations, damages or malfunctions of such an extent that safe operation of the joint cannot be guaranteed for the orthopedic device, the second element and therefore the orthosis element that is non-detachably connected to it and individually adapted to the wearer must be replaced in orthopedic devices of the prior art. This results in high levels of expenditure in terms of cost, production and time, and also means that the orthosis is not available to the wearer for a certain period of time, namely the production time of the respective component to be replaced. This is disadvantageous from a therapeutic perspective and in terms of the level of comfort experienced when wearing. This problem is solved by the design according to the invention as it is only necessary to remove a standard component, namely the respective contact element, from the second element and replace it with an intact contact element.

The orthopedic device is preferably an ankle orthosis. It is especially preferable if the first element is a lower leg element and the second element a foot stirrup.

In a preferred embodiment, the at least one end stop element comprises at least one spring element, at least one damping element and/or at least one static end stop.

Preferably, at least two contact elements are fastened on the second element such that they can be detached and the joint comprises at least two end stop elements, the applied force of each one being introduced into at least one contact surface of at least one contact element. The end stop elements can be designed to be identical or different. It is particularly advantageous if the at least two end stop elements act in different directions so that a force countering the dorsal flexion is applied by the first end stop element and a force countering the plantar flexion is applied by the second element when the contact surface is in contact with the respective end stop element. Due to the fact that different contact elements are provided for different end stop elements, the material input required during replacement is particularly low. For example, if only one of the contact elements is worn down or has been rendered unusable through use, only this one contact element need be replaced, while the other contact element, which does not yet prevent proper use of the orthosis, need not be replaced.

In an alternative embodiment, it is of course possible to detachably arrange only a single contact element on the second element, said contact element comprising two contact surfaces into each of which the force of at least one end contact element is introduced. When replacing the corresponding contact element, a larger component must then be removed and replaced by an intact component.

In a preferred embodiment, each end stop element features at least one force transmission element with a contact area which rests on the contact surface of the respective contact element when the force applied by the end stop element is introduced into the contact surface of the contact element. Such a force transmission element may be, for example, a tappet, a pin or a mandrel, which is spring-loaded and can be displaced along a displacement direction if the end stop element is spring-loaded or damped At the end facing away from the end stop element, such a force transmission element preferably features a contact area which is brought to rest on the contact surface of the contact element.

The at least one contact surface is formed in such a way that the force applied by the at least one end stop element is always perpendicular to the contact surface, irrespective of a position of the second element relative to the first element. This ensures an optimal force transmission and also avoids shear forces and lateral accelerations. This is especially, but not exclusively, advantageous if the end stop element used is to be compressed along a compression direction in order to exert the force it generates. If the force transmission element is the pin or tappet mentioned above, the compression direction is preferably identical to the displacement direction of the force transmission element. When swivelling the second element relative to the first element, the end stop element is compressed by the second element, wherein a force is introduced into the end stop element. It has been proven advantageous if this force always acts in the compression direction of the end stop element, irrespective of the position of the second element relative to the first element and thus also irrespective of the position of the second element relative to the end stop element. This can be achieved with a careful selection of the geometric form and contour of the at least one contact surface of the contact element, and the form and contour of the contact area of the force transmission element. Both designs are coordinated so as to achieve the desired result.

It is especially preferable if the form and contour of the at least one contact surface of the contact element and the form and contour of the contact area of the force transmission element are coordinated in such a way that they both come into contact along a line, the so-called load line. The longer this line, the lower the pressure acting at each individual point and the greater the reduction in wear and tear. The load line preferably extends in the same plane as the swivel axis of the joint, i.e. preferably in the frontal plane in the case of joints for ankle orthoses.

It is advantageous if the at least one contact element is made of a harder material than the second element, preferably hardened steel. This reduces wear and deformation of the contact element, so that replacement and exchange of a deformed and worn contact element is rarely necessary.

In an alternative embodiment, the at least one contact element is made of a softer material than the second element, preferably ELADUR (polyurethane elastomer based on polyether). This embodiment ensures that a force transmission element, for example, through which the force applied by the at least one spring element is introduced into the contact surface of the contact element, is not subject to wear and does not become deformed and unusable. Rather, the softer material of the contact element ensures that the contact element must be replaced once worn and from time to time. As such, a complicated replacement of other components, especially a force transmission element, can be avoided.

The contact element preferably contains an elastic material or is even predominantly or entirely made of an elastic material. Here, at least one component can be made of a harder material. To this end, for example, a metal pin can be inserted or introduced into the elastic material to prevent a deformation.

The contact surface is preferably designed to be concave. In this case, the contact surface of the contact element is preferably designed in the shape of a slight groove, particularly a longitudinal groove. It can thus guide the contact area of a force transmission element and prevent transverse acceleration and displacement of the force transmission element.

It is especially preferable if the contact area is designed to be convex and to have a radius of curvature that corresponds to a radius of curvature of the contact surface of the contact element. This reinforces the guidance of the contact area of the force transmission element on the contact surface of the contact element. In addition, the coordinated, preferably identical, radii of curvature ensure that the size of the surface where the two components come into contact with each other is as large as possible, thereby keeping the forces acting at the individual points, i.e. specifically the pressure at individual points, as low as possible. As a result, the forces transmitted from the at least one end stop element via the force transmission element to the contact element are distributed across as large an area as possible, thereby reducing the pressure at individual points. This also prevents excessive wear and increases the service life of the individual components, particularly the contact element.

It is advantageous if the at least one contact element is screwed onto the second element. This may be achieved, for example, using one or multiple grub screws.

In a preferred embodiment, the at least one contact element and the second element are correspondingly designed and formed in such a way that the contact element can only be fixed to the second element in a single or limited number of orientations. This is particularly beneficial if the contact surface of the contact element is structured and not designed to be flat. In this case, an incorrect orientation of a newly arranged contact element on the second element can lead to malfunctions and undesired pressure spikes on the contact surface of the contact element. Moreover, an asymmetrical design of the contact element, for example, in order to ensure that it is only arranged on the second element in one orientation, reduces the manufacturing and replacement effort.

The joint is preferably designed in such a way that the contact element is visible in at least one orientation and/or position of the first element relative to the second element without dismantling the joint. It is therefore easy to monitor wear without having to disassemble the joint.

The at least one contact element preferably has two sides that are spaced apart from each other and between which the second element of the joint is arranged. Preferably, each of the sides features a bore that can be brought into overlap with a recess or bore of the second element. In this state, a pin or bolt is pushed or inserted through the overlapped bores, thereby connecting the at least one contact element to the second element. Preferably, a screw, such as a shaft screw, is used instead of a bolt or a pin. In this case, at least one of the bores through which the screw is guided features an inner thread, which is designed to correspond with an outer thread of the screw. It is especially preferable for all bores to have such an inner thread.

Preferably, the sides of the at least one contact element each feature more than one bore which can be brought into overlap with a corresponding number of bores or recesses in the second element. It is then possible to use more than one pin, bolt or more than one screw to connect the at least one contact element to the second element. Of course, different elements can be used, such as a pin and a screw.

BRIEF DESCRIPTION OF THE DRAWINGS

In the following, an example of an embodiment of the present invention will be explained in more detail by way of the attached figures: They show:

FIG. 1—the schematic representation of a foot stirrup for a joint for an ankle orthosis according to a first example of an embodiment of the present invention, FIG. 2—the foot stirrup from FIG. 1 in a rotated view, FIG. 3—an enlarged section from FIG. 2, FIG. 4—a part of a foot stirrup in a three-dimensional view, FIG. 5—the schematic sectional representation through a part of a joint according to the prior art, FIG. 6—the representation from FIG. 5 for a joint according to an example of an embodiment of the present invention, FIG. 7—the schematic representation of various embodiments of a corresponding joint, FIG. 8—the schematic representation of a further embodiment in a sectional view and a side view, FIG. 9—the schematic representation of a further example of an embodiment in two different views, and FIG. 10—the schematic representation of a contact element in different views.

DETAILED DESCRIPTION

Figure 4:
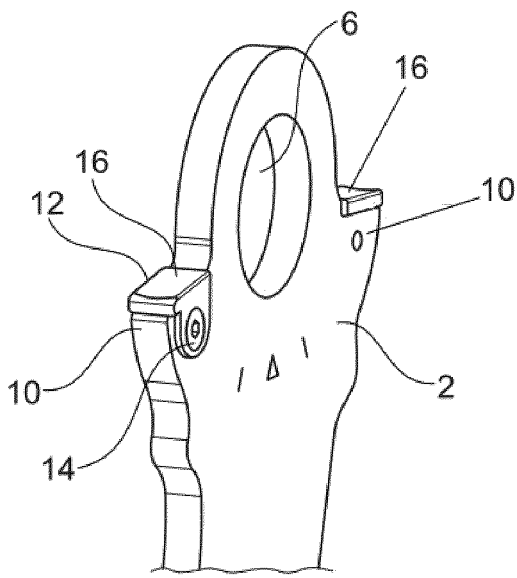

FIG. 1 shows a foot stirrup 2 for a joint for an orthopedic device in the form of a joint orthosis according to an example of an embodiment of the present invention.

It features a fixing element 4 on which, for example, a foot part of an ankle orthosis can be arranged. This is preferably done in a non-detachable manner.

In the upper area of the foot stirrup 2 is an opening 6 through which a swivel axis passes in the mounted state, about which the foot stirrup 2 shown can be swivelled about a lower leg element, not depicted. The foot stirrup 2 features markings 8 which should enable an optimal adjustment to the needs of the wearer of the ankle orthosis as well as ensuring that adjustments, once set, are reproducible.

The foot stirrup 2 has two shoulders 10, one contact element 12 being arranged on each. In the example of an embodiment shown, the contact element 12 is fixed to the shoulder 10 by a screw 14 such that it can be detached.

FIG. 2 depicts the foot stirrup 2 from FIG. 1 in a side view. The contact element 12 that is fixed with the screw 14 can be seen on the shoulder 10.

FIG. 3 depicts an enlarged section. The screw 14 with which the contact element 12 is arranged on the shoulder 10 can be clearly seen. The contact element 12 has a contact surface 16, which is designed to be flat in the example of an embodiment shown and on which, for example, a force transmission element rests, by way of which the force applied by the at least one spring element, not depicted here, is introduced into the contact element 12.

FIG. 4 shows the upper part of the foot stirrup 2 from FIGS. 1, 2 and 3 in a schematic, three-dimensional view. One can see the opening 6, the two shoulders 10 as well as the contact element 12 arranged via the screw 14. Unlike in FIG. 3, however, the contact surface 16 is designed to be concave and in this case forms a longitudinal groove that extends in the radial direction in relation to a swivel axis to be passed through the opening 6. This ensures that the contact between the force transmission element, not depicted, and the contact surface of the contact element is as effective as possible.

Figures 5, 6:
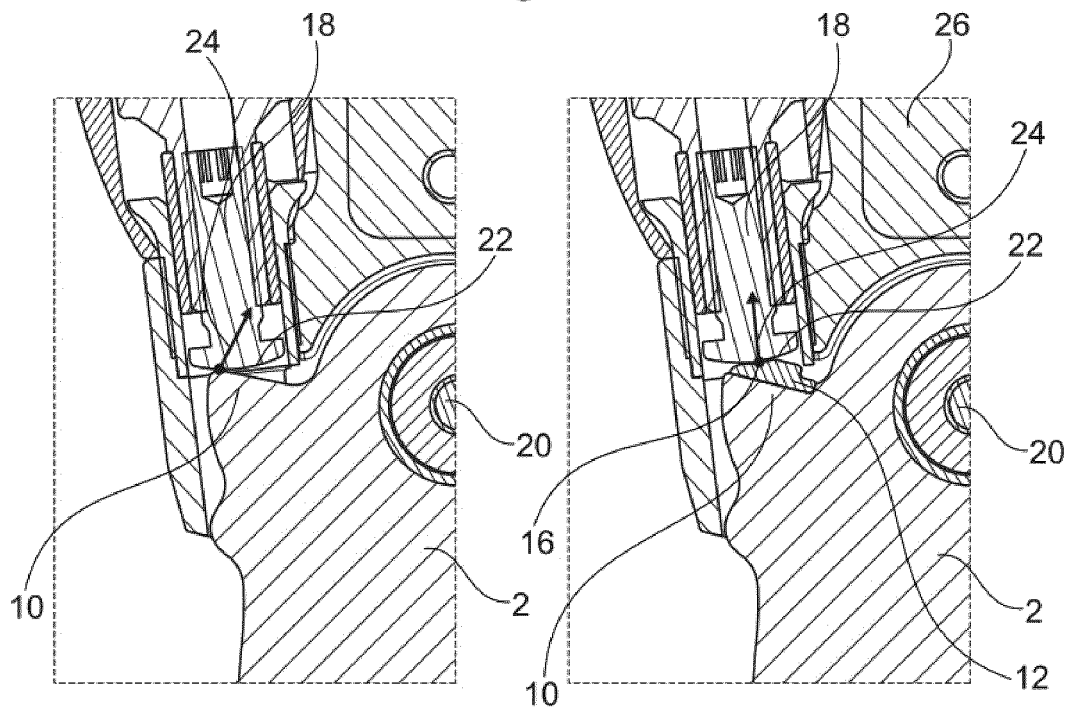

This situation is depicted in FIGS. 5 and 6. One can see the force transmission element 18 via which a force exerted by a spring element, not depicted, is applied to a shoulder 10 of a foot stirrup 2 of the prior art. If the foot stirrup 2 is swivelled about the swivel axis 20 in the clockwise direction, the shoulder 10 will move upwards, the force transmission element 18 is also displaced upwards and the spring element, not depicted, thus compressed. The representation in FIG. 5 is not a joint according to the invention, as the foot stirrup 2 is not designed with a contact element 12. Rather, the shoulder 10 forms the contact surface, which comes into mechanical contact with a contact area 22 of the force transmission element 18, said area being designed to be convex. Due to the design of the contact surface of the shoulder 10 and the contact area 22 of the force transmission element 18, a force is applied to the force transmission element 18 along the arrow 24 when the foot stirrup 2 is swivelled in the clockwise direction about the swivel axis 20. However, this force and the arrow 24 are not parallel to a longitudinal extension of the force transmission element 18, which corresponds to the displacement direction of the force transmission element 18 and the compression direction of the spring element, not depicted.

FIG. 6 depicts the same situation with a foot stirrup 2 for a joint according to an example of an embodiment of the present invention. The contact element 12 is arranged on the shoulder 10, said contact element comprising a contact surface 16 that is correspondingly shaped to the contact area 22 of the force transmission element 18. Irrespective of the position and orientation of the foot stirrup 2 relative to the lower leg element 26, a force is applied to the force transmission element 18 when the foot stirrup 2 is swivelled about the swivel axis 20 in the clockwise direction, wherein said force runs along the arrow 24 and is thus always applied parallel to the displacement direction of the force transmission element 18 and therefore to the compression direction of the spring element, not depicted.

Figure 7:
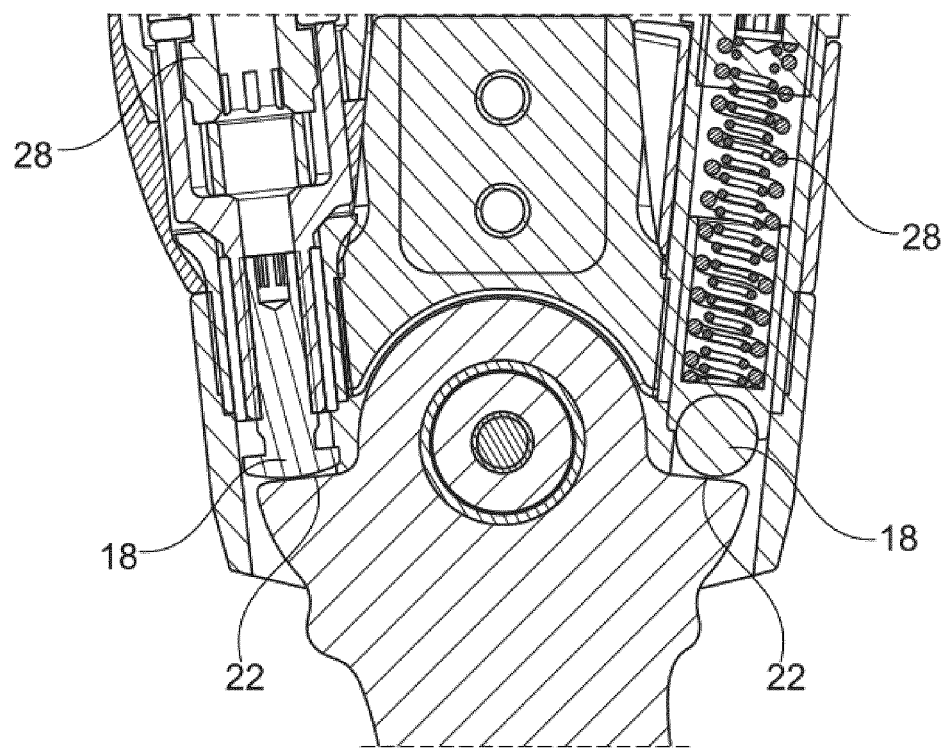

FIG. 7 schematically depicts various forms of spring elements 28 and various forms of force transmission elements 18. While the left-hand area shows the force transmission element 18 from FIGS. 5 and 6, which features the previously described contact area 22, the force transmission element 18 in the right-hand example is designed in the shape of a ball, the contact area 22 having a much smaller surface in this case. Even though no contact elements 12 are depicted in the example of an embodiment shown in FIG. 7, they are nevertheless there and have not been drawn solely for reasons of clarity.

Figure 8:
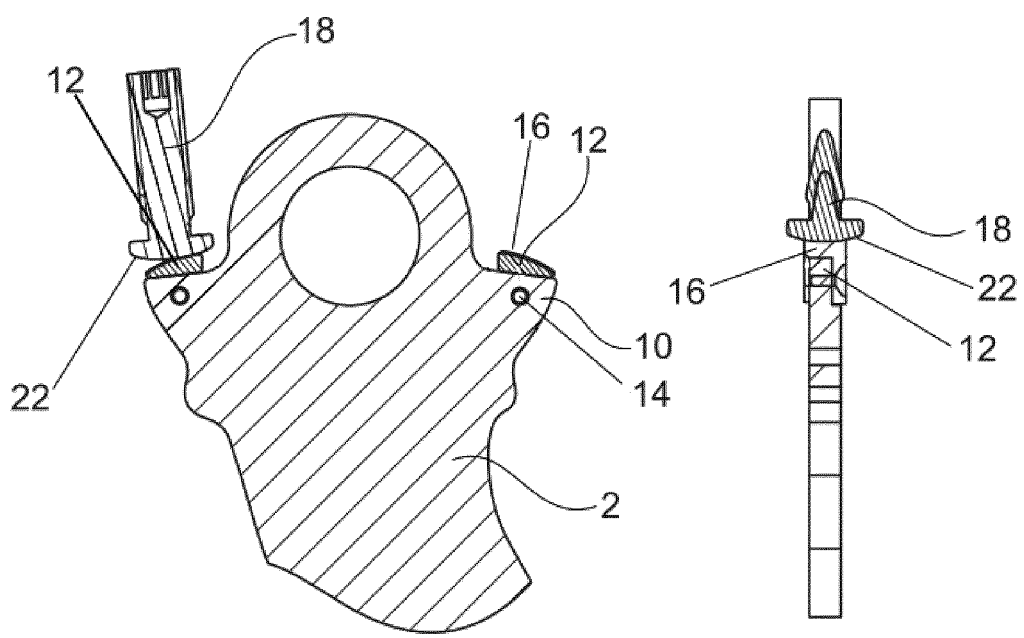

The left-hand representation in FIG. 8 shows the foot stirrup 2 on which two contact elements 12 are arranged, which are positioned by means of the screw 14 on the shoulder 10. It can be seen that the contact elements 12 comprise a curved contact surface 16 that corresponds to the curvature of the contact area 22 of the force transmission element 18. In the left-hand part of FIG. 8, this corresponds to the representation from FIG. 6. The right-hand part of FIG. 8 features a representation that corresponds to the representation from FIGS. 2 and 3. Here too, one can see the force transmission element 18, which has a curved contact area 22. The section shown in the right-hand part of FIG. 8 corresponds to that of a frontal plane and it can be seen that the contact surface 16 of the contact element 12 is also curved in this direction. As a result of this design, the contact between the contact area 22 of the force transmission element 18 and the contact surface 16 of the contact element 12 is always linear, so that the pressures acting at the respective points can be kept as low as possible.

Figure 9:
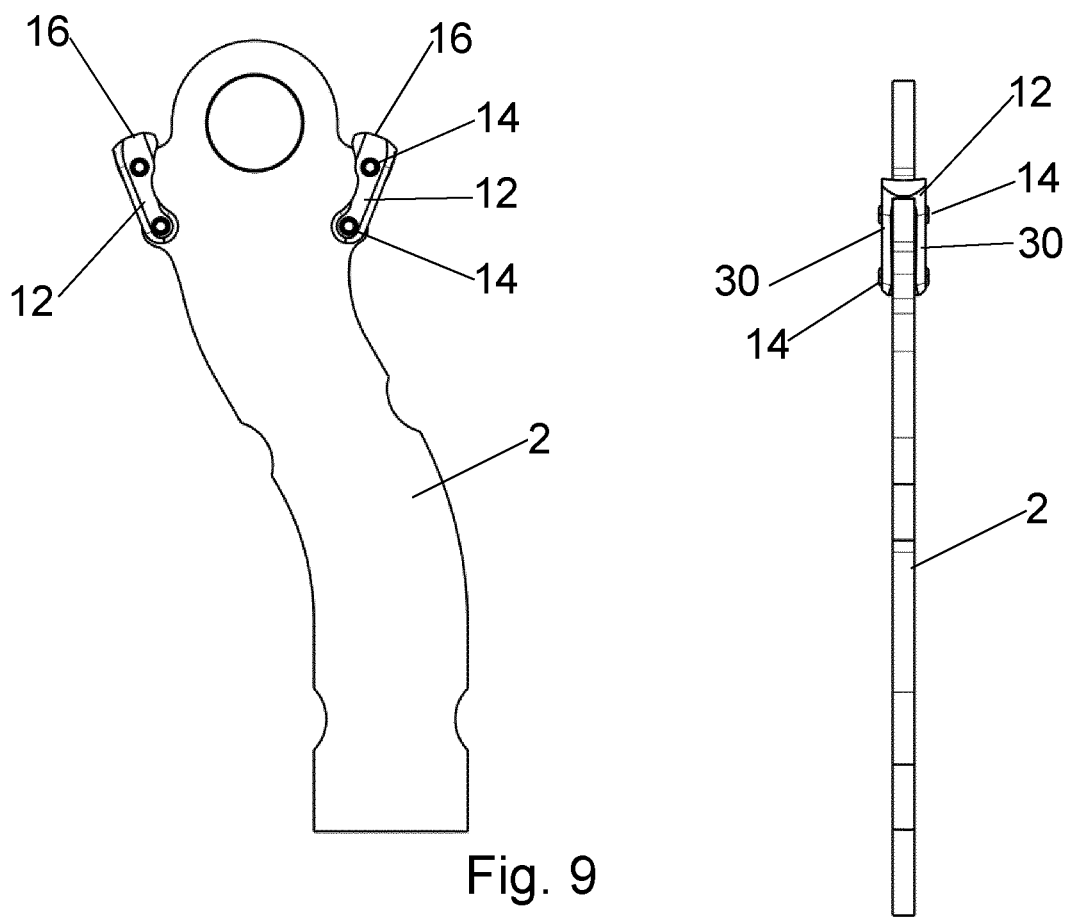

FIG. 9 depicts a further embodiment of a foot stirrup 2 on which two contact elements 12 are also located. These elements each have a contact surface 16 and are each fixed to the foot stirrup 2 by two screws 14 in the example of an embodiment shown. Alternatively, the contact elements 12 may also be fixed to the foot stirrup by two pins or bolts, or by a screw 14 and a pin or bolt. The right-hand representation in FIG. 9 shows the foot stirrup 2 with one of the contact elements 12. The contact element 12 has two sides 30 arranged on both sides of the foot stirrup 2. The two sides 30 as well as the foot stirrup 2 each feature bores or recesses that are brought into overlap with each other in the embodiment shown, such that the screws 15 can be inserted or screwed through them. This results in a symmetrical fixing of the contact element 12 to the foot stirrup 2, thereby achieving a particularly even load and therefore a high resistance to wear.

Figure 10:
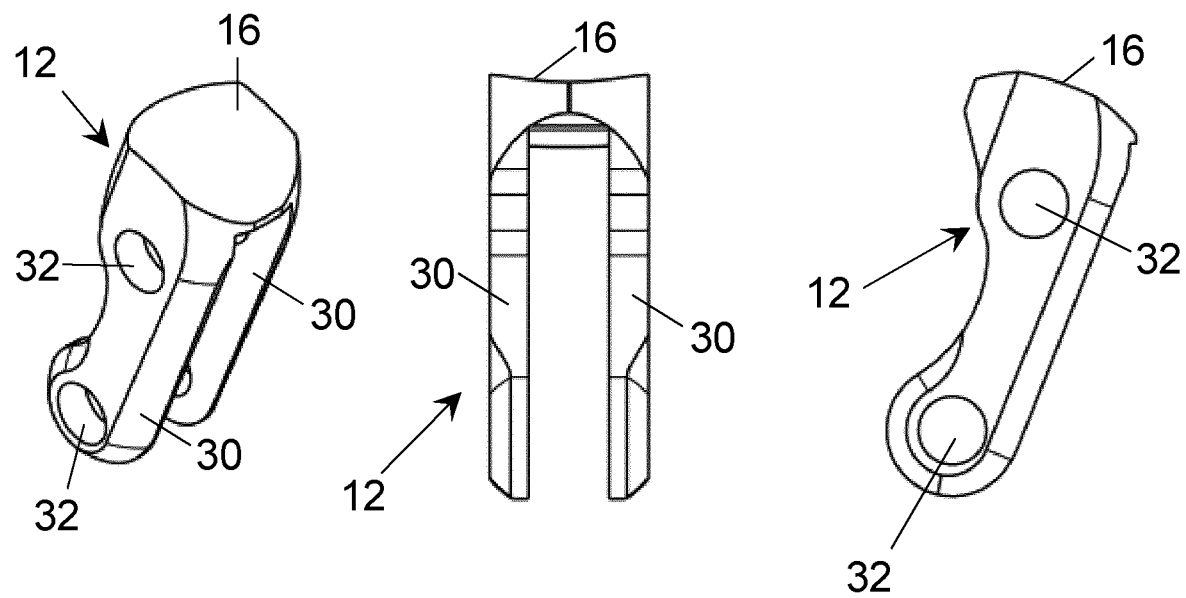

FIG. 10 depicts a contact element 12 in three different representations. It comprises the contact surface 16, which is designed to be slightly concave, as can be seen particularly clearly in the middle representation of FIG. 10. The contact element 12 comprises the two sides 30, each of which has two bores 32.

REFERENCE LIST

2—foot stirrup
4—fixing element
6—opening
8—marking
10—shoulder
12—contact element
14—screw
16—contact surface
18—force transmission element
20—swivel axis
22—contact area
24—arrow
26—lower leg element
28—spring element
30—side
32—bore

The invention claimed is:

1. A joint for an ankle orthosis, wherein the joint comprises:
a lower leg element with at least one end stop element, and
a foot stirrup which is mounted on the lower leg element such that the foot stirrup is configured to be swivelled and configured to be brought into contact with the at least one end stop element by swivelling the foot stirrup relative to the lower leg element, wherein the at least one end stop element then counters a further swivelling of the foot stirrup relative to the lower leg element with a force,
characterized in that at least one contact element is detachably fixed on the foot stirrup such that the at least one contact element is configured to be detached, said at least one contact element having at least one contact element contact surface, wherein the at least one end stop element comprises either at least one spring element or at least one damping element to apply the force and counter the further swivelling of the foot stirrup relative to the lower leg element, wherein the further swivelling of the foot stirrup relative to the lower leg element occurs when the force applied by the at least one spring element or at least one damping element is overcome, wherein the at least one end stop element further comprises at least one force transmission element comprising a contact area that rests on the at least one contact element contact surface when the at least one contact element contact surface comes into contact with the at least one end stop element.

2. The joint according to claim 1, wherein the at least one contact element is screwed onto the foot stirrup.

3. The joint according to claim 1, wherein the at least one contact element and the foot stirrup are correspondingly designed and formed in such a way that the at least one contact element can only be fixed to the foot stirrup in a single orientation.

4. The joint according to claim 1, wherein at least two contact elements are detachably fixed on the foot stirrup and the joint comprises at least two end stop elements, wherein the at least two contact elements each has at least one element contact surface that is configured to be brought into contact with each of the at least one end stop elements.

5. The joint according to claim 1, wherein the joint is designed in such a way that the at least one contact element is visible in at least one orientation and/or position of the lower leg element relative to the foot stirrup without dismantling the joint.

6. The joint according to claim 1, wherein the at least one contact element contact surface is formed in such a way that the force that counters the further swivelling applied by the at least one stop element is always perpendicular to the at least one contact element contact surface irrespective of a position of the lower leg element relative to the foot stirrup.

7. The joint according to claim 1, wherein the at least one contact element is made of a harder material than that of the foot stirrup.

8. The joint according to claim 1, wherein the at least one contact element is made of a softer material than that of the foot stirrup.

9. The joint according to claim 8, wherein the at least one contact element contains an elastic material.

10. The joint according to claim 1, wherein the at least one contact element contact surface is designed to be concave.

11. The joint according to claim 1, wherein the contact area is designed to be convex and preferably has a radius of curvature that corresponds to a radius of curvature of the contact element contact surface of the at least one contact element.

12. A joint for an ankle orthosis, wherein the joint comprises:
   a lower leg element with at least two end stop elements selected from the group of a spring element or damping element;
   a foot stirrup which is mounted on the lower leg element such that the foot stirrup is configured to be swivelled and is configured to be brought into contact with the at least two end stop elements by swivelling the foot stirrup relative to the lower leg element, wherein the at least two end stop elements then counters a further swivelling of the foot stirrup relative to the lower leg element with a force, wherein the further swivelling of the foot stirrup relative to the lower leg element occurs when the force applied by the spring element or the damping element is overcome;
   wherein at least two contact elements are detachably fixed on the foot stirrup, each of the at least two contact elements has at least one contact element contact surface that is configured to be brought into contact with one of the at least two end stop elements; and
   wherein each of the at least two end stop elements further comprises at least one force transmission element with a contact area that rests on the at least one contact element contact surface.

13. A joint for an ankle orthosis, wherein the joint comprises:
   a lower leg element with at least one end stop element which includes at least one of a spring element or damping element;
   a foot stirrup which is mounted on the lower leg element such that the foot stirrup is configured to be swivelled and is configured to be brought into contact with the at least one end stop element by swivelling the foot stirrup relative to the lower leg element, wherein the at least one end stop element then counters a further swivelling of the foot stirrup relative to the lower leg element with a force applied by the spring element or the damping element,
   wherein at least one contact element is detachably fixed on the foot stirrup such that the at least one contact element is configured to be detached, the at least one contact element has at least one contact element contact surface, wherein the further swivelling of the foot stirrup relative to the lower leg element occurs when the force applied by the spring element or the damping element is overcome.

14. The joint according to claim 13, wherein the at least one contact element contact surface is formed in such a way that the force that counters the further swivelling applied by the at least one stop element is always perpendicular to the contact element contact surface irrespective of a position of the lower leg element relative to the foot stirrup.

15. The joint according to claim 13, wherein the at least one contact element is made of hardened steel.

16. The joint according to claim 13, wherein at least two contact elements are detachably fixed on the foot stirrup and the joint comprises at least two end stop elements, wherein the at least two contact elements each has at least one contact element contact surface that is configured to be brought into contact with each of the at least one end stop elements.

17. The joint according to claim 13, wherein each of the at least one end stop elements further comprises at least one force transmission element with a contact area that rests on said at least one contact element contact surface.

* * * * *